United States Patent
Unverzagt et al.

[11] Patent Number: 6,110,897
[45] Date of Patent: Aug. 29, 2000

[54] ANTIINFLAMMATORY CELL ADHESION INHIBITORS

[75] Inventors: Carlo Unverzagt, Munich; Gregor Kuznik, Rott am Lech; Gerhard Kretzschmar, Eschborn, all of Germany

[73] Assignee: Glycorex AB, Lund, Sweden

[21] Appl. No.: 08/948,294

[22] Filed: Oct. 10, 1997

Related U.S. Application Data

[60] Provisional application No. 60/028,563, Oct. 10, 1996.

[51] Int. Cl.$^7$ .............................. A61K 31/70; C07H 15/00
[52] U.S. Cl. .................................. 514/25; 514/54; 514/61; 514/62; 536/17.2; 536/18.5; 536/55; 536/55.1; 536/55.2; 536/55.3
[58] Field of Search .................................. 514/25, 54, 61, 514/62; 536/17.2, 18.5, 55, 55.1, 55.2, 55.3

[56] References Cited

FOREIGN PATENT DOCUMENTS

92/22563  12/1992  WIPO .
93/24505  12/1993  WIPO .

OTHER PUBLICATIONS

Giannis *Angew. Chem. Int. Ed. Engl.* 1994, 33(2), 178–180, month not available.

A. Giannis, "Die Sialyl–Lewis–X–Gruppe und ihre Analoga als Liganden fur Selektine", *Angew. Chem.*. vol. 106:188–191, (1994), months not available.

Nelson et al., "Higher–Affinity Oligosaccharide Ligands For E–Selectin", *J. Clin. Invest.*, vol. 91:1157–1166, (1993), months not available.

Cavallo et al. *Carbohydrate Research* Oct. 1993, 248, 251–265.

Heavner *Drug Discovery Today* Jul. 1996, 1(7), 295–304.

*Primary Examiner*—Kathleen K. Fonda
*Attorney, Agent, or Firm*—Foley & Lardner

[57] ABSTRACT

The invention relates to compounds of formula Ix and Ia:

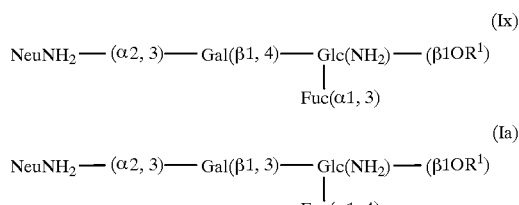

wherein (Ix) comprises the regioisomeric form sLe$^x$ and (Ia) comprises the regioisomeric form sLe$^A$, and R$^1$ is a lipophilic radical formed from aliphatic or cycloaliphatic units, or a sugar residue which is capped by a β1-O-linked aliphatic or cycloaliphatic unit at the reducing end of the terminal sugar. The compounds of the present invention are useful as inhibitors of increased cell-cell adhesion as well as useful in treating diseases associated with increased cell-cell-adhesion. The compounds of the present invention are also incorporated into pharmaceutical compositions.

17 Claims, 5 Drawing Sheets

Figure 3: a) $CuBr_2$, $Bu_4NBr$, $DMF-CH_2Cl_2$ (71 %); b) NIS, triflic acid, Z-aminohexanol, $CH_3CN$ (89 %); c) $NaCNBH_3$, $HCl-Et_2O$, THF (75 %); d) 1. ethylene diamine, n-butanol 80°C, 4h; 2. $Ac_2O$, methanol, ethyl acetate (98 %); e) $BF_3-OEt_2$, molecular sieves 4Å, $CH_2Cl_2$; f) NaOMe, MeOH (e-f: 47 %); Z = benzyloxycarbonyl.

Figure 4: a) sialic acid aldolase b) 1. MeOH, Amberlyst 15 H$^+$; 2. Ac$_2$O-pyridine, 3. TMS-SMe, TMS-OTf; 13a (70 %), 13b (79 %), 13c (73 %).

ANTIINFLAMMATORY CELL ADHESION INHIBITORS

This application is a continuation of Ser. No. 60/028,563 filed Oct. 10, 1996.

The invention relates to novel mimetics of oligosaccharides preferably of derivatives of sialyl-Lewis$^X$ (sLe$^X$) and sialyl-Lewis$^A$ (sLe$^A$), with improved action as inhibitors of cell adhesion, a process for the preparation of these compounds, and their use as pharmacological active compounds and as as diagnostics, and pharmaceuticals which contain these compounds.

BACKGROUND OF THE INVENTION

The binding of selectins, a group of cell surface lectins, to carbohydrate ligands like sialyl-Lewis$^X$ (sLe$^X$) and sialyl-Lewis$^A$ (sLe$^A$), is mediating the attraction of several groups of leukocytes to areas of inflammation (review: S. R. Watson, Adhes. Recept. Ther. Targets 1996, 61–73, Editor A. M. Horton, CRC, Boca Raton, Fla.). This has stimulated research to investigate the use of carbohydrates and their mimetics as potential drugs to prevent the adhesion and subsequent migration of leukocytes to the affected tissues in several acute and chronic inflammatory diseases.

The major natural ligands of the selectins are the sialyl Lewis$^X$ (sLe$^X$) and sialyl-Lewis$^A$ (sLe$^A$) determinants found on the termini of various glycolipids and glycoproteins. Synthetic variations of the functional groups of sLe$^X$ and sLe$^A$ have led to a more detailed knowledge about structure-activity-relationships of the functional groups involved in binding to selectins. FIG. 1 shows the essential structural requirements in sLe$^X$ depicted in bold. The structure of sLe$^A$ is derived from sLe$^X$ by interchange of the NeuAc-($\alpha$2,3)-Gal($\beta$1,4)- and Fuc($\alpha$1,3)-residues on the GlcNAc moiety.

It is known that the acid function present in the sialic acid moiety is crucial and can be replaced, i.e. by sulfate groups. Furthermore, the fucose and some of the galactose hydroxyl groups are essential. The hydroxyl groups and the acetamido group in the sialic acid moiety are believed to be not necessary for binding to the selectin receptors (Review: S. A. Mousa, Drugs of the Future 1996, 21(3), 283).

The course of a number of acute and chronic disorders is unfavorably affected by the excessive adhesion of leucocytes and their infiltration into the tissue. These disorders include, for example, rheumatism, reperfusion injuries such as myocardial ischemia/infarct (MI), acute pneumonia after operative intervention, traumatic shock and stroke, psoriasis, dermatitis, ARDS (adult respiratory distress syndrome) and the restenosis occurring after surgical intervention (for example angioplasty).

A very promising therapeutic starting point is therefore the attempt to employ the tetrasaccharides sLe$^{X/A}$ in various administration forms or mimetics thereof having a modified structure as antagonists for the modulation or suppression of excessive leucocyte adhesion and to employ them for the alleviation or cure of said disorders.

The natural ligand having the structure of sLe$^X$ has already been successfully used in animal experiments in P-selectin-dependent lung injuries (M. S. Mulligan et al., Nature 1993, 364, 149) and in myocardial reperfusion injuries (M. Buerke et al., J. Clin. Invest. 1994, 93, 1140). In primary clinical trials in acute pneumonia the compound should be employed in a dose of 1 to 2 grams per day per patient (communication of Cytel Corp./La Jolla (Calif.) in the 2nd Glycotechnology Meeting/CHI in La Jolla/U.S.A. on May 16–18th 1994). This high dose of active compound is in agreement with the, as is known, weak affinity of the natural sLe$^{X/A}$ ligands for the selectin receptors. Thus sLe$^X$ in all known in vitro test systems inhibits cell adhesion to selectin receptors only at a relatively high concentration in the range of IC$_{50}$=1 to 3 mM.

Higher affinity ligands for the selectins have been prepared, which have even more complex structures than sLe$^X$, higher molecular weights and higher expense with respect to the time and money needed to make substantial amounts of material available (examples are given in Tetrahedron 1995, 51(47), 13015; Angew. Chem. 1996, 108 (16), 1949). On the other hand, the mimetics of sLe$^X$ and sLe$^A$ of lower molecular weight thus far described, exhibit equal or lower receptor affinities compared to the natural saccharides (Drugs of the Future 1996, 21(3), 283).

SUMMARY OF THE INVENTION

The object of the invention is to provide lower molecular weight carbohydrate receptor blockers with respect to the structure shown in FIG. 1, a simple process for their preparation, and pharmaceuticals prepared from these which meet the requirements mentioned.

This object is achieved according to the invention by the simple cleavage of the two acetamido functional groups present in the sialic acid and N-acetylglucosamine moieties present in oligosaccharides which contain the sLe$^X$ and sLe$^A$ structures. This cleavage provides the unmasked derivatives of sLe$^X$ and sLe$^A$ saccharides of reduced molecular weight and can be carried out in a single preparative step in good yield.

Surprisingly, the unmasked derivatives sLe$^X$ and sLe$^A$ saccharides according to the invention bind to E- and P-selectins more strongly than the natural ligands and the corresponding derivatives in which only one of the respective acetamido groups is cleaved. These improved binding properties of the compounds according to the invention can be employed for the prophylaxis, therapy and diagnosis of disorders which are characterized by excessive cell-cell-adhesion.

DETAILED DESCRIPTION OF THE INVENTION

The invention thus relates to a compound of the formula (I), compound (Ia) being the regioisomeric sLe$^A$ form of compound (Ix) which has the sLe$^X$ type structure,

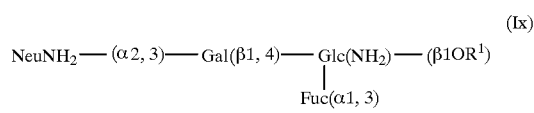

-continued

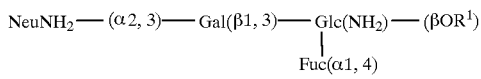

in which

R¹ is a lipophilic radical formed from aliphatic or cycloaliphatic units, or a sugar residue which is capped by a β1-O-linked aliphatic or cycloaliphatic unit at the reducing end of the terminal sugar.

Preferably,

R¹ is a lipophilic radical formed from aliphatic units, or a monosaccharide sugar residue which is capped by a β1-O-linked aliphatic or cycloaliphatic unit at the reducing end.

The present invention further relates to a process for the preparation of compound (I), which is distinguished in that a compound of the formula (II)

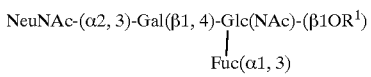

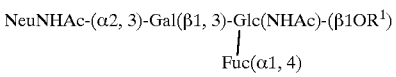

in which R¹ has the meanings mentioned, is reacted with a base. Preferably the base is a tetraalkylammoniumhydroxide. The present invention further relates to a pharmaceutical containing a compound of the formula (I) or its pharmaceutically acceptable salts or acids and, if appropriate, pharmaceutical auxiliaries.

The compound of the formula (I) can in particular be used for the preparation of a pharmaceutical for the prevention or cure of diseases which are caused by increased cell-cell adhesion.

The compound (I) is further suitable for the production of a composition for the diagnosis of diseases which accompany increased cell-cell adhesion and for the preparation of a synthetic vaccine.

In the following, the invention is described in detail, in particular in its preferred embodiments. The invention is furthermore determined by the contents of the patent claims.

Synthesis of the Compounds (I), Precursors (II) and Reference Compounds (III)

The compounds of the formula (I),

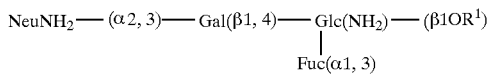

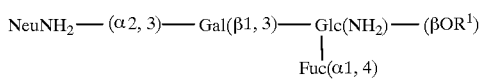

in which R¹ is a lipophilic radical formed from aliphatic or cycloaliphatic units or a sugar residue which is capped by a β1-O-linked aliphatic or cycloaliphatic unit at the reducing end of the terminal sugar, can be prepared from the precursors of the formula (II) known from the literature in a simple manner by basic saponification of the acetamido groups in the sLe$^A$ or in the sLe$^X$ moiety in one single preparative step.

Examples of suitable syntheses of the oligosaccharide precursors (II) are found in Angew. Chem. 1994, 106,(20), 2186, for sLe$^X$ type compounds where R¹ is a hexanolamine spacer, in J. Carbohydr. Chem. 1994, 13, 641 for the sLe$^A$ type compounds. Further examples of suitable syntheses of oligosaccharide precursors (II) are found in Angew. Chem. 1995, 107, 453, 569, i.a the 1βO-allyl glycoside of sLe$^X$ and sLe$^X$-βO1,3-galactosyl-1βO-ethyl glycosides.

Figure 1:
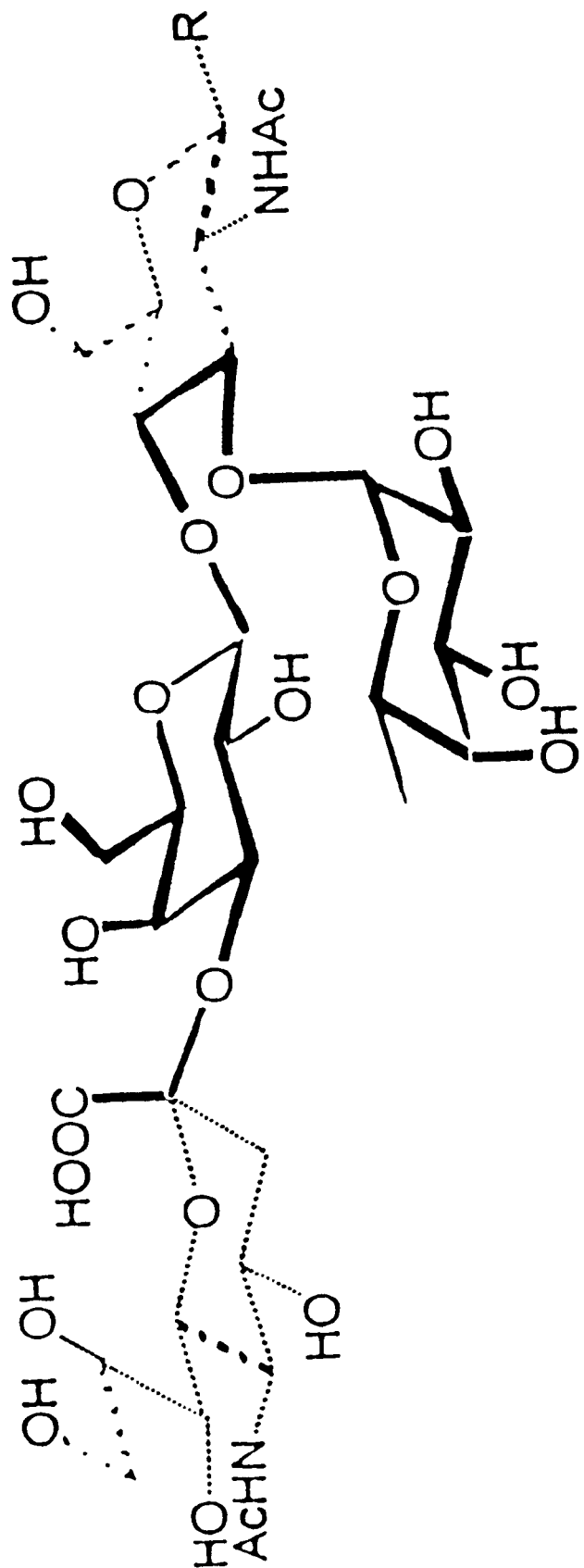
FIG. 1 shows key polar groups for selectin binding.
Figure 2:
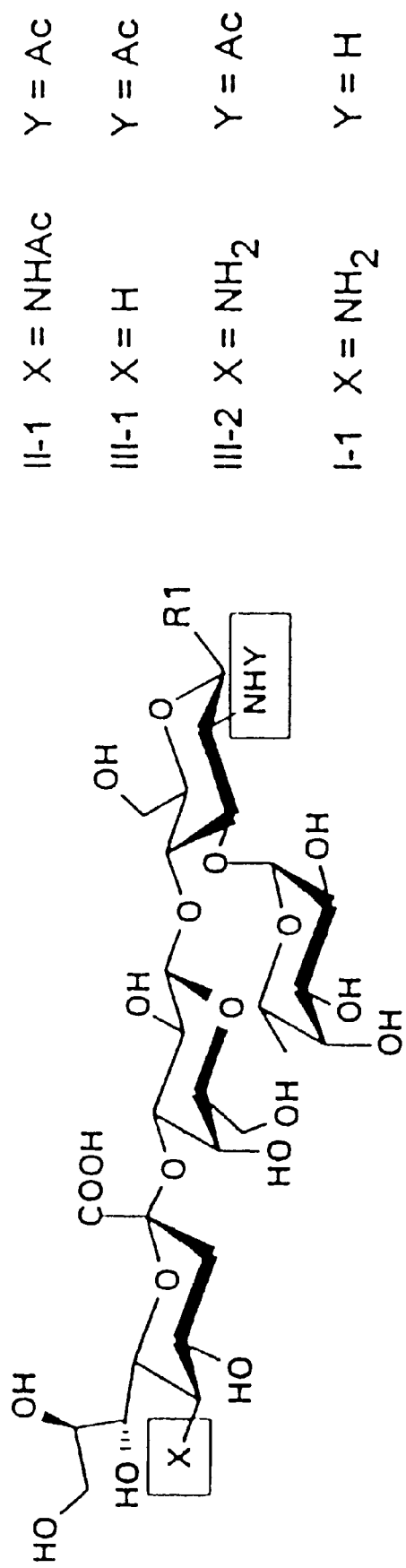
FIG. 2 shows tetrasaccharides modified at C-5 of sialic acid and at C-2 of GlcNAc.

In order to illustrate the improved biological activity of a compound of the formula (I) compared to closely related compounds in which either the 5-position of the sialic acid or the 3-position of the N-acetylglucosamine is modified or unmasked, respectively, the Le$^X$ tetrasaccharides (III) were prepared as reference compounds from readily available building blocks activated as thioglycosides or trichloroacetimidates (FIG. 2).

Figure 3:
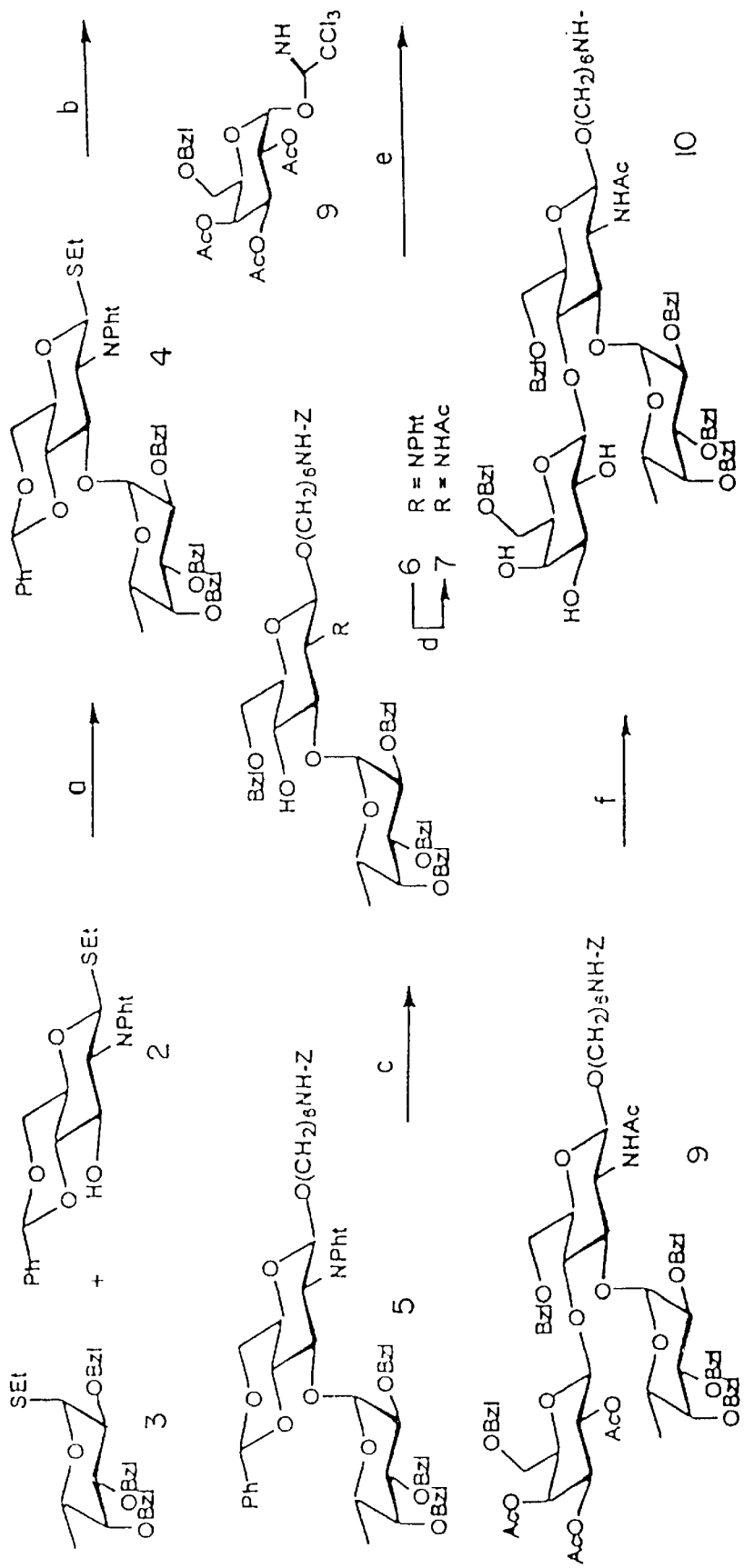
FIG. 3 shows synthesis of the Le$^X$ trisaccharide.

Initially, the Le$^X$ trisaccharide was assembled followed by sialylation with modified sialic acid donors as shown in FIG. 3. Coupling of thioglycoside 2, available in four steps from glucosamine hydrochloride (Carbohydr. Res. 1985, 139, 105), and thioethylfucoside 3, gave the disaccharide 4 in 71% yield. The fucosyl donor 3 was selectively activated in the presence of a thioethyl moiety in the acceptor. Subsequently the benzyloxycarbonyl-hexanolamine spacer was introduced by activating disaccharide 4 with NIS-triflic acid. Regioselective reduction of the benzylidene acetal 5 with sodium cyanoborhydride gave the acceptor 6 which was dephthaloylated with ethylenediamine/n-butanol. Typically, the deprotection was complete after 4 hrs at 80° C. whereas side products appeared after 8 hrs of reaction time. Chemoselective N-acetylation furnished the acceptor 7 and subsequent elongation with the galactosyl imidate 8 gave the trisaccharide 9. The three acetyl groups were released by Zemplén deprotection and the resulting triol 12 was used for regioselective sialylations at position 3".

Figure 4:
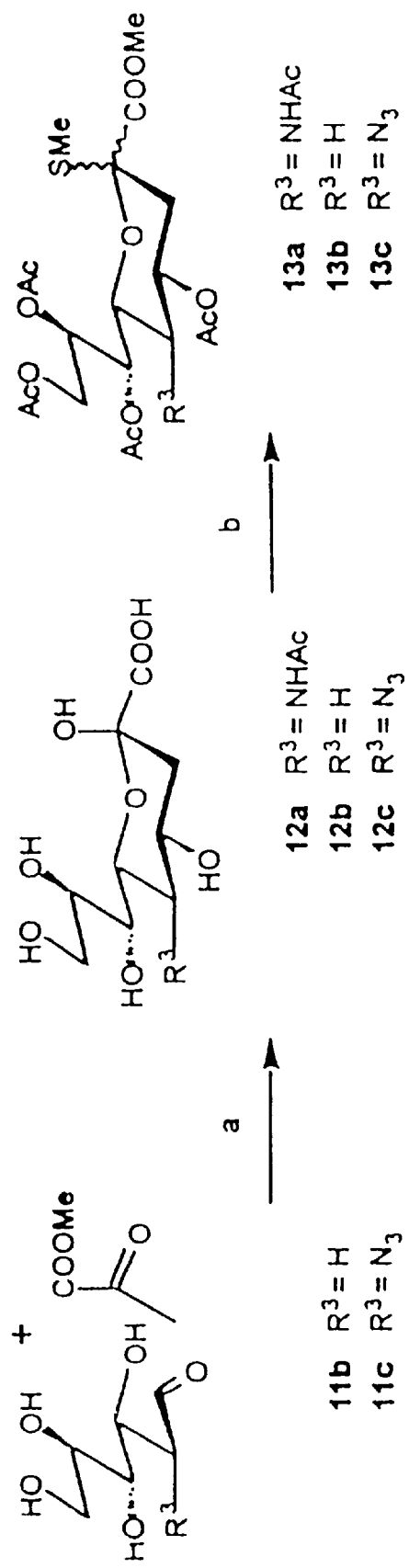
FIG. 4 shows synthesis of the thiomethyl donors for coupling to the Le$^X$ trisaccharide.

The modified sialic acids 12b and 12c were obtained enzymatically from 2-deoxy mannose 11b or 2-azido mannose 11c and pyruvate using sialic acid aldolase analogously as described in Tetrahedron 1990, 46, 201 and Carbohydr. Res. 1989, 188, 201 and in FIG. 4.

Conversion to the thiomethyl donors 13a–c was performed in a three step procedure:

esterification in methanol catalyzed by dry ion exchange resin
  acetylation
  thiomethylation with TMS-SMe/TMS-triflate.

This reaction sequence afforded the sialyl donors 13a–c in good yields. Regioselective α-(2-3)-sialylation of the Lex trisaccharide 10 was conducted under the conditions described in the literature (Angew. Chem. 1994, 106, 2186) and afforded the tetrasaccharide 14a in 54% yield for the N-acetyl neuraminyl donor 13a. For the modified donors 13b and 13c, however, the yields were significantly lower.

Figure 5:
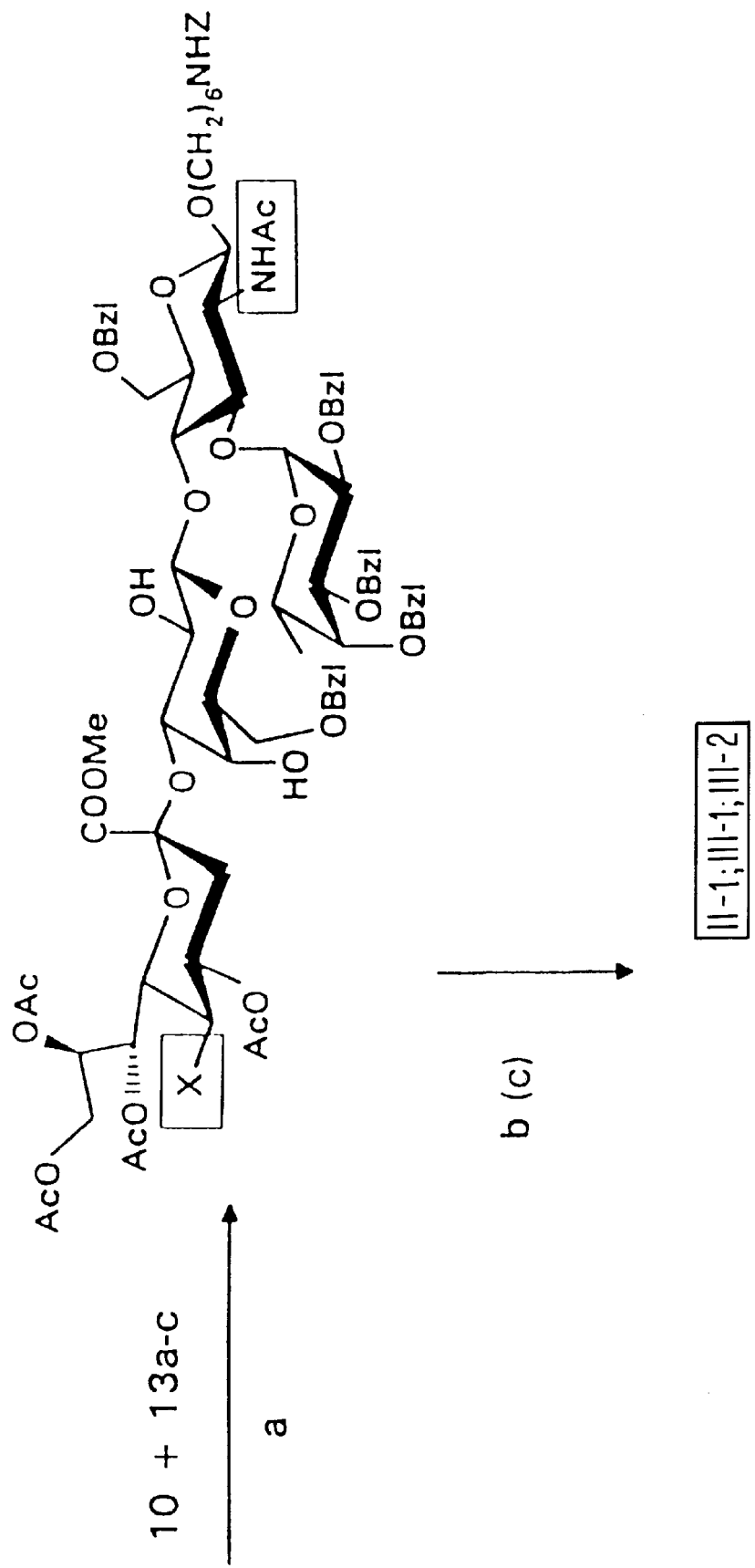
FIG. 5 shows the final steps of the synthesis of the tetrasaccharides II-1 (X=N-acetyl), III-1 (X=H) and III-2 (X=NH$_2$).

FIG. 5 describes the deprotection reactions: Compound 14a and 14b can be deprotected under the same conditions as for the deblocking of 14a using a three step procedure with formic acid as the hydrogen donor in the catalytic hydrogenation. The final basic treatment is needed to open the lactone ring that is formed in the deacetylation step. Despite the increased acid sensitivity of the 5-deoxy sialoside III-1 compared to the N-acetyl derivative II-1, the acidic conditions are well tolerated. However, the neuraminyl compound III-2 decomposes in the presence of formic acid. The highly acid sensitive sialoside III-2 was deprotected by mild catalytic transfer hydrogenation with ammonium formate as the hydrogen source.

The base stability of saccharides II is very high. Therefore, the basic hydrolysis of the two acetamides in II-1 with tetrabutylammonium hydroxide at 95° C. gives the pure lyso-sLe$^X$ tetrasaccharide derivative I-1 in 53% yield under non-optimized reaction conditions, after purification by column chromatography on a sephadex support.

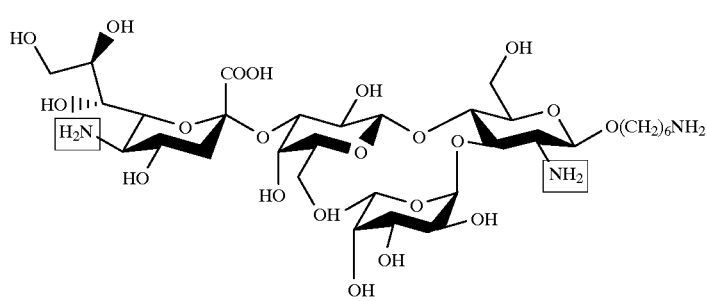

I-1

The very high base stability of unprotected saccharides II offers the potential to prepare other selectin ligands, i.e. the diamine pentasaccharide I-2 from the corresponding precursor molecule II-2 by deacetylation of the acetamido functions.

ment of inflammatory processes, preferably of myocardial infarct and ischemia, post-infarct syndrome, shock lung of the adult, septic shock, stroke, acute and chronic organ rejection, vasculitis, inflammatory diseases of the skin,

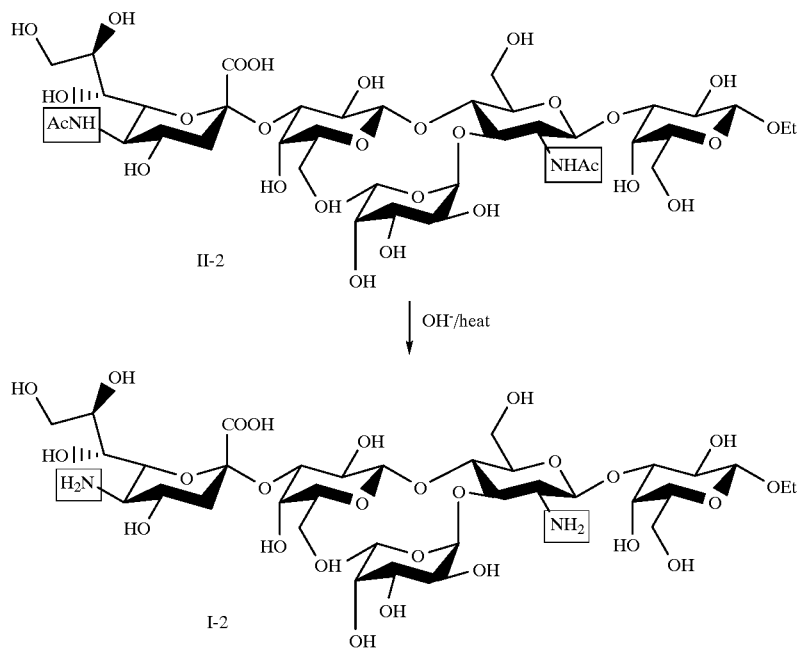

The compounds of formulae (I) are suitable as pharmacologically active substances, in particular as active compounds for the prophylaxis or cure of diseases which are caused by increased cell-cell adhesion. The compounds according to the invention in particular show improved efficacy in the inhibition of cell adhesion mediated by selectin receptors.

The carbohydrate conjugates must have no disadvantageous side effects in applications in vivo. Thus, in the case of intravenous administrations, hemolytic and undesired immunogenic properties, for example, are to be avoided. The enzymes of the blood clotting cascade must not be activated, in order to exclude the formation of thrombi.

The carbohydrate conjugates according to the invention and their physiologically tolerable salts are very highly suitable on account of their valuable pharmacological properties for use as therapeutics in mammals, in particular man. The pharmaceuticals are preferably suitable for the prophylaxis and/or therapy of diseases which proceed with involverheumatoid arthritis, restenosis after angioplasty and also metastasizing tumors.

The pharmaceuticals according to the invention are in general administered intravenously, orally or parenterally or as implants, but rectal application is also possible in principle. Suitable solid or liquid pharmaceutical preparation forms are, for example, granules, powders, tablets, coated tablets, (micro)capsules, suppositories, syrups, emulsions, suspensions, aerosols, drops or injectable solutions in ampoule form and also preparations having protracted release of active compound, in whose preparation excipients and additives and/or auxiliaries such as disintegrants, binders, coating agents, swelling agents, glidants or lubricants, flavorings, sweeteners or solubilizers are customarily used. Frequently used excipients or auxiliaries which may be mentioned are e.g. magnesium carbonate, titanium dioxide, lactose, mannitol and other sugars, talc, lactoprotein, gelatin, starch, vitamins, cellulose and its derivatives, animal and vegetable oils, polyethylene glycols and solvents, such as, for example, sterile water, alcohols, glycerol and polyhydric alcohols. The pharmaceutical preparations are preferably prepared and administered in dose units. In the case of solid dose units, tablets, capsules and suppositories are preferred.

Further pharmaceutical preparations include salts of compounds I formed with organic or inorganic acids in order to improve the bioavailability or in order to supplement the inflammatory activity. Examples for inorganic acids are hydrochloric or sulfuric acid. Examples for organic acids are citric acid, formic acid, acetic acid, salicyclic acid, ibuprofen®, naproxen® and the like.

For treatment of a patient, different daily doses are necessary depending on the efficacy of the compound, manner of administration, nature and severity of the disease, and age and body weight of the patient. Under certain circumstances, however, higher or lower daily doses may also be appropriate. The daily dose can be administered both by single administration in the form of an individual dose unit or else as several small dose units and also by multiple administration of subdivided doses at certain intervals. The daily dose to be administered may additionally be dependent on the number of receptors expressed during the course of the disease. It is conceivable that in the initial stage of the disease only a few receptors are expressed on the cell surface and accordingly the daily dose to be administered is lower than in severely ill patients.

The pharmaceuticals according to the invention are prepared by bringing the carbohydrate conjugate into a suitable administration form using customary excipients and, if appropriate, additives and/or auxiliaries.

Primary assays for investigation of the action of compounds (I) on cell adhesion to recombinant soluble selectin fusion proteins:

The preparation of soluble E- and P-selectin-IgG fusion proteins, composed of the extracellular portions of human selectins E and P and the human immunoglobulin (IgG) heavy chain hinge, CH2 and CH3 regions, has been described in Cell 1991, 67, 35. These recombinant proteins contain the signal sequence, the lectin-like domain, the EGF (epidermal growth factor) repeat domain and six (E-selectin) and two (P-selectin) of the CR-like (complement regulatory) domains. The recombinant proteins obtained from transfected COS cells according to standard procedures (current protocols in molecular biology 1994, John Wiley & Sons) were adsorbed on anti-human-IgG-antibodies immobilized on ELISA (enzyme-linked immunosorbent assay) plates. Adhesion of labelled HL60 tumor cells was quantitatively measured in a cytofluoro-meter. The specific cell binding in the presence of inhibitors (I) was calculated compared with nonspecific binding to the CD4-IgG fusion protein.

The testing results which prove the inhibitory potency towards E- and P-selectins are shown in Table 1.

The inhibitory potency of (II-1) is only slightly improved by removal of the acetamido or acetyl group in the derivatives (III-1) and (III-2), respectively. Surprisingly, the binding affinity to P-selectin is significantly enhanced by a factor of 12.5 in the fully deacetylated (I-1). In a recent study published in J. Clin. Invest. 1993, 91(3), 1157–1166, leukocyte adhesion to immobilized P-selectin-Ig was reported to be poorly blocked by oligosaccharides related to sLe$^X$ and sLe$^A$ and neither azido nor amino substitutions at C-2 of GlcNAc enhanced the blocking ability. Similar results were obtained in cell-free ELISAs, but there a 5fold enhanced inhibitory potency of the sLe$^X$(GlcNH$_2$) compared to sLe$^X$ in the E-selectin-Ig competitive binding studies was achieved, albeit on much lower concentration levels (IC$_{50}$s of 77 µM and 380 µM, respectively) in the cell-free systems. This trend for E-selectin compares well with the significant improvement of the IC$_{50}$ of (I-1) over the reference compound (II-1). Without being bound to any particular theory, the present inventors believe that the improvement achieved in binding to P-selectin therefore may be due to a synergistic effect caused by the additional amino group C-5 in the sialic acid moiety, by virtue of additional polar interactions with the receptor protein. It should therefore be possible to increase the inhibitor potency of other oligosaccharides in a similar manner, e.g., the diamine pentasaccharide I-2 that can be prepared from the corresponding molecule II-2 by deacetylation of the acetamido functions.

The following examples further illustrate the invention. Percentage data relate to the weight. Mixing ratios in case of liquids relate to the volume if no other details are given.

EXAMPLE 1

Synthesis of 2-Amino-4-O-[3-O-[5-amino-3,5-dideoxy-D-glycero-α-D-galactononulopyranosyl]-β-D-galactopyranosyl]-1-[6-aminohexyl]-2-deoxy-3-O-[α-L-fucopyranosyl]-β-D-glycopyranose (I-1)

A solution of 4 ml 25% tetramethylammoniumhydroxide in methanol is evaporated to dryness under vacuum and the residue taken up in 0.5 mL of water. This solution is added to a solution of 21.6 mg of compound II-1 (23.5 mmol) in 0.5 ml water. After 4 days at 95° C. the reaction is terminated as monitored by thin layer chromatography (TLC) in isopropanol/1 M NH$_4$OAc, 4:1). After cooling to room temperature the solution is diluted to 10 ml with water and neutralized to pH 7.0–8.0 with 50% acetic acid. Lyophylisation gives a crude product mixture (751.6 mg) which is subjected to chromatography on Sephadex (column diameter Ø 3.5 cm, length 25 cm, eluent 0.1 M NH$_4$HCO$_3$ solution) to separate the product from the tetramethylammoniumacetate. The product fraction (60.0 mg) is dissolved in 10 ml water and rechromatographed on Carboxymethyl-Sephadex (column diameter Ø 1 cm, length 3 cm; support CM Sephadex C25 gel from Sigma-Aldrich, eluent water with increasing gradient of ammoniumacetate solution 0.1 M to 1 M.) Prior to charging the column with the material, the column was eluted to dryness. At 0.3 M–0.4 M ammoniumacetate concentration the product is eluted (lyophilised material 24.6 mg) which can be further purified by elution with 0.1 M NH$_4$HCO$_3$ solution. Final yield of the highly pure product I-1 is 10.4 mg (53%)

R$_f$=0.43 (isopropanol/1 M NH$_4$OAc, 4:1). [a]$^{22}_D$=−33.3° (0.7, H$_2$O). C$_{33}$H$_{61}$N$_3$O$_{21}$ (835.85). ESI-MS (0.01 M NH$_4$OAc/ACN): M$_{calc.}$=835.4. M$_{found}$=836.6 (M+H)

$^1$H-NMR (500 MHz, D$_2$O): d=5.14 (d, J$_{1,2}$=3.0 Hz, 1H, H-1'), 4.78 (m, 1H, H-5'), 4.45 (d, J$_{1,2}$=8.0 Hz, 1H, H-1"), 4.37 (d, J$_{1,2}$=8.0 Hz, 1H, H-1), 4.03 (m, 1H, H-3"), 3.98 (m, 1H, H-6a), 3.89 (m, 1H, H-4"), 3.89 (m, 1H, aCH$_2$), 3.88 (m, 1H, H-8$^N$), 3.87 (m, 2H, H-9a$^N$,H-9b$^N$), 3.85 (m, 1H, H-6b), 3.84 (m, 1H, H-3'), 3.83 (m, 1H, H-4), 3.79 (m, 1H, H-2'), 3.78 (m, 1H, H-7$^N$), 3.74 (m, 1H, H-4'), 3.64 (m, 2H, H-6a", H-6b"), 3.64 (m, 1H, H-5"), 3.63 (m, 1H, aCH$_2$), 3.59 (m, 1H, H-3), 3.54 (m, 1H, H-6$^N$), 3.55 (m, 1H, H-5), 3.52 (m, 1H, H-2"), 3.47 (m, 1H, H-4$^N$), 2.95 (m, 2H, kCH$_2$), 2.81 (m, 1H, H-5$^N$), 2.80 (m, 1H, H-2), 2.68 (dd, J$_{gem}$=12.8 Hz, J$_{vic}$=3.5 Hz, 1H, H-3eq$^N$), 1.69 (dd, J$_{vic}$=12.1 Hz, 1H, H-3ax$^N$), 1.63 (m, 2H, eCH$_2$), 1.61 (m, 2H, bCH$_2$), 1.37 (m, 4H, g,dCH$_2$), 1.13 (d, J$_{5,6}$=6.1 Hz, 3H, H-6').

$^{13}$C-NMR (125 MHz, D$_2$O): d=171.0 C-1$^N$, 100.0 C-1, 99.3 C-1", 97.4 C-1', 97.2 C-2$^N$, 77.2 C-3, 73.0 C-5, 73.0

C-$6^N$, 73.0 C-5", 73.0 C-3", 70.9 C-4, 69.9 C-4', 69.9 C-$8^N$, 67.8 aCH$_2$, 67.8 C-$4^N$, 66.8 C-3', 66.8 C-2", 65.8 C-$7^N$, 65.8 C-2', 64.8 C-4", 64.7 C-5', 60.5 C-$9^N$, 59.5 C-6", 57.5 C-6, 55.5 C-2, 50.3 C-$5^N$, 37.8 C-$3^N$, 36.8 kCH$_2$, 26.4 bCH$_2$, 24.3 eCH$_2$, 22.2, g,dCH$_2$, 13.0 C-6'.

EXAMPLE 2

Synthesis of Compound (I-2)

Deacetylation of the precursor compound (II-2) is carried out as described for the preparation of (I-1) in example 1 using the freshly prepared tetramethylammoniumhydroxide solution.

EXAMPLE 3

Selectin Cell Adhesion Assays

The activity of compounds (I), (II) and (III) was measured in adhesion assays as the inhibition of the binding of promyelocytic leukemia HL60 cells (ATCC CRL 1964) to recombinant solid phase bound selectin-fusion proteins. Genetic constructs for expression of extracellular portions of the human selectins E and P, joined to human immunoglobulin heavy chain hinge, CH$_2$ and CH$_3$ regions were obtained from B. Seed, Massachusetts General Hospital, Boston, U.S.A. The soluble E- and P-selectin-IgG fusion proteins contain the signal sequence, the lectin-like domain, the EGF repeat domain and six (E-selectin) and two (P-selectin) of the complement regulatory-like domains. CD4-IgG served as a negative control. Recombinant proteins were expressed as soluble proteins after DEAE/dextran facilitated plasmid DNA trans-fection into COS cells according to standard procedures. The 96well round bottomed ELISA plates (Maxi-sorp, Nunc, Kamstrup, Denmark) were precoated for 1 h at room temperature (RT) with 100 μl/well of 10 μg/ml goat-anti-human-Ig (Cappel, Durham, U.S.A.) in 50 mM Tris-HCl (pH 9.5). After washing with PBS, plates were blocked for 0.5 h with 150 μl/well of 1% BSA in PBS. Next, plates were coated with fusion proteins by incubating the plates for 1.5 h with either 100 μl/well CD4-IgG, E-selectin-IgG or P-selectin-IgG fusion protein in COS-cell culture supernatants diluted to the same fusion protein content (1–2 μg/ml) as determined by an Ig specific ELISA. 100 μl/well of Fc-receptor blocking buffer (1 mg/ml g-globulin, Sigma, Deisenhofen, FRG) in binding buffer (see below) was added to prevent HL60 cell binding to immobilised goat anti human Ig antibody via Fc receptors. After one PBS wash, 40 μl/well binding buffer (50 mM Hepes, pH 7.5, 100 mM NaCl, 100 μM MgCl$_2$. 100 μM MnCl$_2$, 100 μM CaCl$_2$, 1 mg/ml BSA) were added together with test compounds or antibodies (see below). Parallel to the preparation of the plates, HL60 cells, grown in DMEM medium with 20% FCS, were washed two times with PBS before incubation for 20 min in Fc-receptor blocking buffer at RT. $10^5$ cells/well in 50 μl Fc-receptor blocking buffer were left to sediment and to adhere for 10 min, before the plates were slowly immersed at a 45° angle in stop buffer (25 mM Tris-HCl, pH 7.5, 100 mM NaCl, 100 μM MgCl$_2$, 100 μM MnCl$_2$, 100 μM CaCl$_2$) to remove all unbound cells. After inverting the plate on filter paper and one repeat of the washing step, 50 μl/well of staining solution (4% formaldehyde, 0.5% Triton X-100, 17 μg/ml Hoechst 33528 DNA dye) was slowly added and incubated at RT for 15 min. The amount of bound cells was quantitated in a cytofluorometer (CytoFluor 2300, Millipore, Bedford, U.S.A.). Specific cell binding was calculated by subtraction of the signals in wells coated with CD4-IgG (nonspecific binding) from the signals in wells coated with selectin-IgG. Assay performance was controlled by using adhesion blocking mouse anti-E-selectin mono-clonal antibody (clone BBIG-E4, R&D systems, Abingdon, UK) and compound II-1 as inhibition controls. IC$_{50}$ values were determined according to the four parameter logistics model. Each IC$_{50}$ determination was repeated on another day at least once.

The results are shown in Table 1:

TABLE 1

Inhibition of HL60 cell adhesion to recombinant E- and P-selectin-IgG fusion proteins. IC$_{50}$ values are concentrations of inhibitors required to block adhesion of 50% of o the cells compared with the negative control.

| Compound | II-1 | III-1 | III-2 | I-1 |
|---|---|---|---|---|
| E-selectin IC$_{50}$ | 1000 μM | 700 μM | 900 μM | 270 μM |
| P-selectin IC$_{50}$ | 2000 μM | 700 μM | 1000 μM | 160 μM |

We claim:

1. A compound selected from the group consisting of:

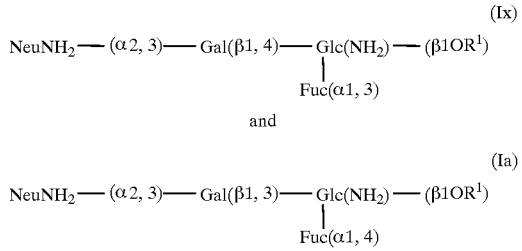

and wherein NeuNH$_2$ is 5-aminoneuraminic acid, and Glc(NH$_2$) is 2-amino-2-deoxyglucose, and R$^1$ is a lipophilic radical formed from aliphatic or cycloaliphatic units, or a sugar residue which is capped by a β1-O-linked aliphatic or cycloaliphatic unit at the reducing end of the terminal sugar.

2. A compound according to claim 1 wherein R$^1$ is a lipophilic radical formed from aliphatic units, or a monosaccharide sugar residue which is capped by a β1-O-linked aliphatic or cycloaliphatic unit at the reducing end of the terminal sugar.

3. A process for preparing a compound according to claim 1 which comprises reacting the compound of formula II,

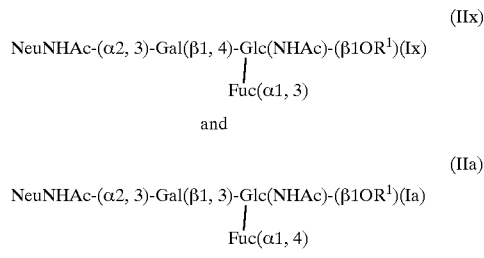

wherein NeuNHAc is 5-N-acetylaminoneuraminic acid, and Glc(NHAc) is N-acetyl 2-amino-2-deoxyglucose, with a strong base.

4. A process preparing a compound according to claim 1, wherein said strong base is a tetraalkylammoniumhydroxide.

5. A pharmaceutical composition comprising a compound according to claim 1 or its pharmaceutically acceptable salt or acid in admixture with a pharmaceutically acceptable excipient.

6. A method of treating a disease associated with increased selectin-mediated cell-cell adhesion comprising administering a therapeutically effective selectin-binding amount of a compound according to claim 1 to a patient in need thereof.

7. A method of diagnosing a disease associated with increased selectin-mediated cell-cell adhesion comprising administering a diagnostically effective selectin-binding amount of a compound according to claim 1 to a patient in need thereof.

8. A compound selected from the group consisting of:

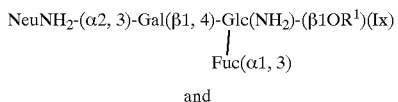

and

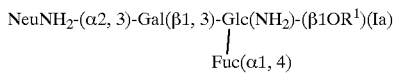

wherein $NeuNH_2$ is 5-aminoneuraminic acid, and $Glc(NH_2)$ is 2-amino-2-deoxyglucose, and $R^1$ is a lipophilic radical formed from aliphatic units, or a monosaccharide sugar residue which is capped by a β1-O-linked aliphatic or cycloaliphatic unit at the reducing end of the terminal sugar.

9. A process for preparing a carbohydrate selectin receptor blocker comprising treating an oligosaccharide with base wherein said oligosaccharide comprises a sialic acid moiety and a N-acetylglucosamine moiety whereby the sialic acid moiety and the N-acetylglucosamine moiety of the oligosaccharide are deacetylated.

10. The process according to claim 9 wherein said oligosaccharide is selected from the group consisting of sialyl-Lewis$^x$ oligosaccharide and sialyl-Lewis$^A$ oligosaccharide.

11. A method for inhibiting selectin-mediated cell-cell adhesion comprising treating cells with an effective selectin-binding amount of a compound according to claim 1.

12. The compound according to claim 1 wherein the compound is 2-amino-4-O-[3-O-[5-amino-3,5-dideoxy-D-glycero-α-D-galactononulopyranosyl]-β-D-galactopyranosyl]-1-[6-aminohexyl]-2-deoxy-3-O-[α-L-fucopyranosyl]-β-D-glucopyranose.

13. The compound according to claim 1 wherein said compound is in the form of an acid salt selected from the group consisting of a hydrochloric acid salt, a sulfuric acid salt a citric acid salt, formic acid salt, acetic acid salt, and a salicylic acid salt.

14. A process for preparing a pharmaceutical composition comprising admixing a compound according to claim 1 with a pharmaceutically acceptable excipient.

15. The process according to claim 3 wherein the compound of formula IIx or IIa is reacted with a strong base at about 95° C.

16. The process according to claim 4 wherein said strong base is tetramethylammoniumhydroxide.

17. The method of treating a disease associated with increased cell-cell adhesion according to claim 6 wherein said diseases are selected from the group consisting of inflammatory processes, myocardial infarction, ischemia, post-infarct syndrome, shock lung of the adult, septic shock, stroke, acute and chronic organ rejection, vasculitis, inflammatory diseases of the skin, rheumatoid arthritis, restenosis after angioplasty and metastasizing tumors.

* * * * *